United States Patent [19]

Thornwald

[11] 4,061,698
[45] Dec. 6, 1977

[54] HUMIDIFIER-NEBULIZER APPARATUS

[75] Inventor: Everett D. Thornwald, Glenview, Ill.

[73] Assignee: Aerwey Laboratories, Inc., Deerfield, Ill.

[21] Appl. No.: 569,229

[22] Filed: Apr. 18, 1975

[51] Int. Cl.² .................. B01F 3/04; A61M 15/00
[52] U.S. Cl. .................. 261/78 A; 128/186; 128/194; 261/122; 261/124; 261/DIG. 65
[58] Field of Search .......... 261/78 A, 122, 124, 261/DIG. 65, 123; 128/186, 188, 192, 194

[56] References Cited

U.S. PATENT DOCUMENTS

| 3,228,526 | 1/1966 | Ciabattari et al. | 261/124 X |
| 3,572,660 | 3/1971 | Mahon et al. | 261/DIG. 65 |
| 3,701,793 | 10/1972 | Schmidt et al. | 261/123 X |
| 3,724,454 | 4/1973 | Brown | 261/DIG. 65 |
| 3,744,771 | 7/1973 | Deaton | 261/DIG. 65 |
| 3,771,721 | 11/1973 | Amerongen | 261/DIG. 65 |
| 3,807,713 | 4/1974 | Cornett et al. | 261/DIG. 65 |
| 3,857,909 | 12/1974 | Huggins | 261/DIG. 65 |
| 3,864,440 | 2/1975 | Giocoechea | 261/DIG. 65 |
| 3,903,216 | 9/1975 | Allan et al. | 261/DIG. 65 |
| 3,913,843 | 10/1975 | Cambio, Jr. | 128/194 X |
| 3,915,386 | 10/1975 | Vora | 128/194 X |

FOREIGN PATENT DOCUMENTS 88,403  4/1960  Denmark .................. 128/194

Primary Examiner—Tim R. Miles
Assistant Examiner—Richard L. Chiesa
Attorney, Agent, or Firm—Fitch, Even, Tabin & Luedeka

[57] ABSTRACT

A humidifier-nebulizer apparatus is disclosed which includes a liquid reservoir having a sterile liquid such as water contained therein, the liquid reservoir having a sealed wall portion adapted to be pierced by the piercing element of an adapter head when mounted on the liquid reservoir. The adapter head may be attached to a source of pressurized gas, such as oxygen, and includes control valve means movable to discharge a nebulized gas-liquid mixture from the adapter head during a nebulizing mode of operation. The control valve means is also adjustable to a position to introduce oxygen into the liquid reservoir in a manner to effect discharge of humidified oxygen through a discharge port on the liquid reservoir.

6 Claims, 9 Drawing Figures

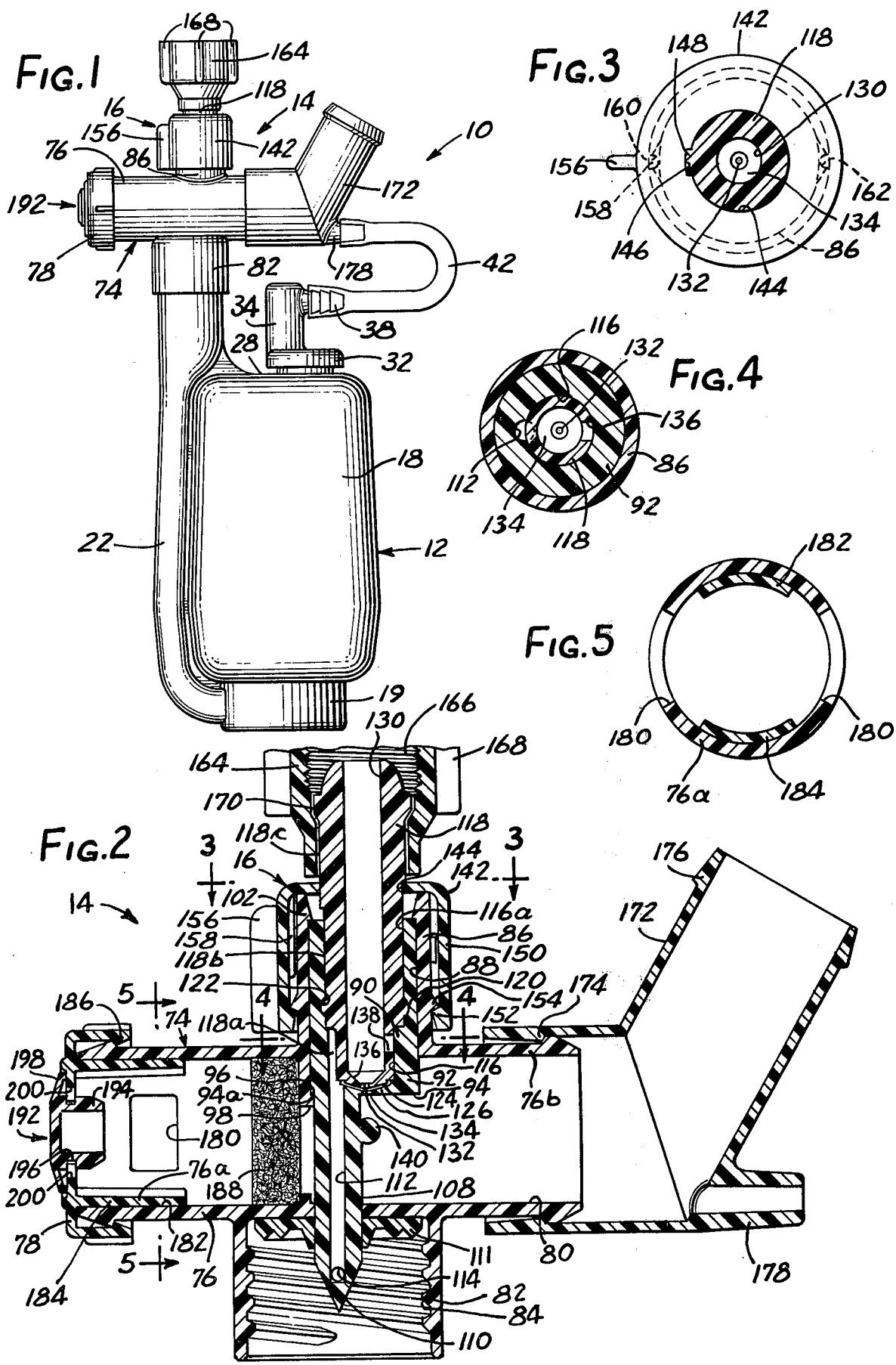

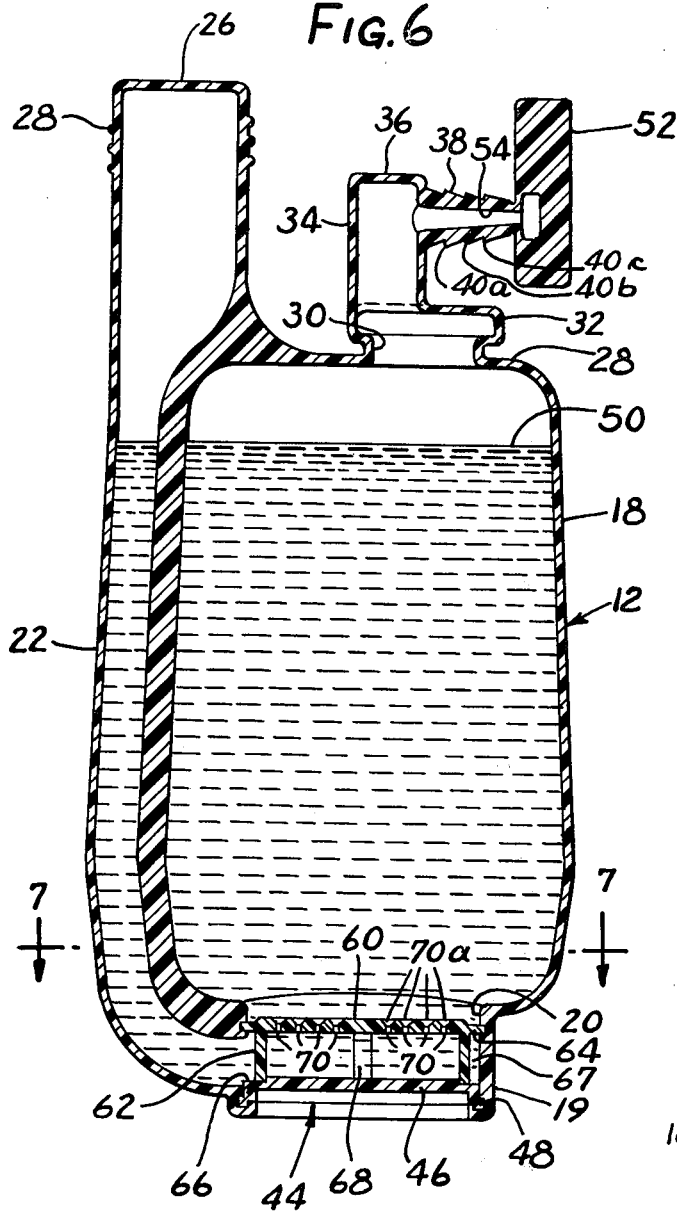
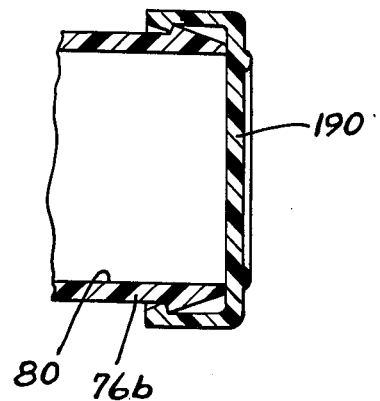
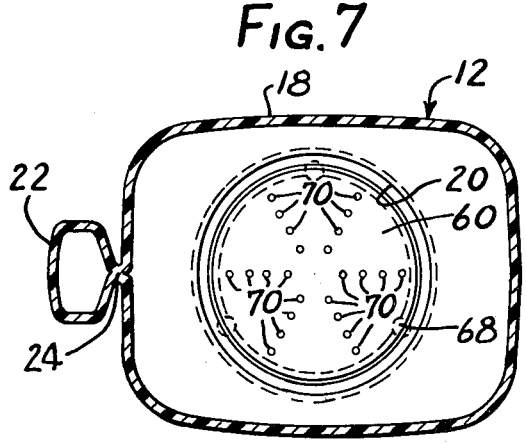
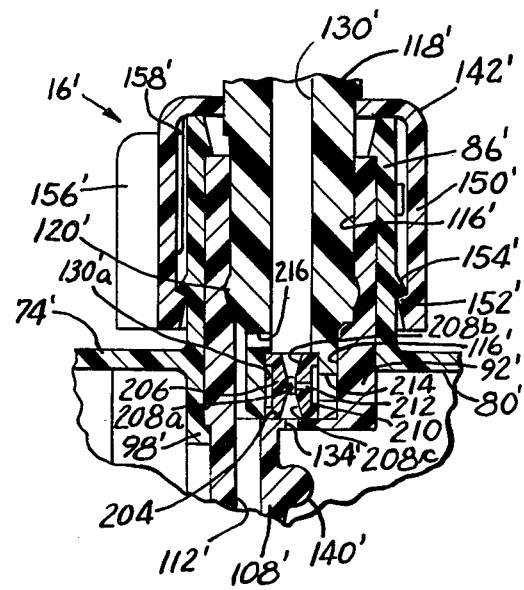

HUMIDIFIER-NEBULIZER APPARATUS

The present invention relates generally to humidifier and nebulizer apparatus, and more particularly to a novel humidifier-nebulizer employing an adapter head which facilitates use of the apparatus as either a humidifier or nebulizer.

It is known in the treatment of persons having respiratory disorders, such as emphysema or asthma, to provide inhalation therapy through the employment of humidifers or nebulizers. In such instances, the person affected with the disorder inhales a gas-liquid mixture from the nebulizer or humidifier. A nebulizer is conventionally employed to introduce a medicinal solution in the form of a fine mist, spray or vapor into a person's respiratory system, with the percentage of liquid in the gas being relatively large as compared with the discharge from a humidifier. The nebulizer effects a breakdown of the liquid particles carried in the gas to a size insuring that the liquid particles reach their intended destination within the person's respiratory system. A humidifier, on the other hand, is effective to moisten the gas discharged in a manner to introduce a moistened gas, such as oxygen, into a person's respiratory system. The gas is moistened so as to prevent desiccation of the respiratory tract or membranes during treatment over a prolonged period.

In the treatment of respiratory disorders, whether the treatment be administered in an institution, such as a hospital, or at home, it is desirable that the patient be able to administer inhalation therapy to himself conveniently and without having to adjust, assemble, or otherwise manipulate complicated apparatus. The present invention provides a humidifier-nebulizer which takes the form of a single unit which a patient may readily and simply adjust for use as either a humidifier or nebulizer.

One of the primary objects of the present invention is to provide a humidifier-nebulizer employing novel adapter head means which provide for simple adjustment to operate the apparatus in either a humidifier or nebulizer mode of operation.

Another object of the present invention is to provide a novel adapter head for use with a liquid reservoir, which adapter head has a body member adapted for connection to a sealed liquid reservoir and a source of pressurized gas, and has selectively movable control valve means operable in a first position to discharge a nebulized gas from the adapter head, and operable in a second position to effect discharge of a humidified gas from a discharge port on the reservoir.

Another object of the present invention is to provide a humidifier-nebulizer apparatus employing a novel liquid reservoir which facilitates ease of manufacture and filling of the reservoir with attendant economic savings.

Still another object of the present invention is to provide a humidifier-nebulizer apparatus which employs a novel liquid reservoir having a sparger member disposed between a gas input tube and a primary liquid reservoir, the sparger member being adapted to provide highly efficient and quiet operation as the gas is introduced into the liquid.

A feature of the present invention lies in the provision of pressure relief means on the adapter head of the humidifier-nebulizer apparatus for preventing harmful affects to the adapter head during pressure buildup in the apparatus when used in a humidifier mode of operation.

Further objects and advantages of the present invention, together with the organization and manner of operation thereof, will become apparent from the following detailed description of the invention when taken in conjunction with the accompanying drawings wherein like reference numerals designate like elements throughout the several views, and wherein:

FIG. 1 is a side elevational view of a humidifier-nebulizer apparatus constructed in accordance with the present invention and shown in a nebulizing mode of operation;

FIG. 2 is an enlarged longitudinal sectional view of the adapter head assembly employed in the apparatus of FIG. 1, the adapter head being shown for use in a nebulization mode of operation;

FIG. 3 is a transverse sectional view taken substantially along the line 3—3 of FIG. 2, looking in the direction of the arrows;

FIG. 4 is a transverse sectional view taken substantially along the line 4—4 of FIG. 2, looking in the direction of the arrows;

FIG. 5 is a sectional view taken substantially along the line 5—5 of FIG. 2, looking in the direction of the arrows;

FIG. 6 is an enlarged longitudinal sectional view of the liquid reservoir used in the apparatus of FIG. 1, the liquid reservoir being in a sealed condition prior to assembly of the adapter head thereon;

FIG. 7 is a transverse sectional view taken substantially along the line 7—7 of FIG. 6 to illustrate the sparger member;

FIG. 8 is an enlarged partial sectional view illustrating the discharge end of the adapter head having a sealing cap mounted thereon for use when the apparatus is used in a humidifier mode of operation; and FIG. 9 is an enlarged partial longitudinal sectional view illustrating an alternative embodiment of a control valve used in the adapter head.

Referring now to the drawings, and in particular to FIG. 1, a humidifier-nebulizer apparatus in accordance with the present invention is indicated generally at 10. The humidifier-nebulizer apparatus 10 includes liquid reservoir means, indicated generally at 12, and adapter head means, indicated generally at 14. As will be described more fully below, the liquid reservoir 12 is adapted to contain a quantity of sterile liquid such as water or a medicinal liquid, and is further adapted to have the adapter head means 14 mounted thereon. In operation, the adapter head means 14 is connected to a source of oxygen or the like (not shown) and includes control valve means, indicated generally at 16, operative between first and second positions to allow use of the humidifier-nebulizer apparatus 10 in either a humidifying or nebulizing mode of operation. In the embodiment illustrated in FIG. 1, the humidifier-nebulizer apparatus 10 is shown for use in a nebulizing mode of operation.

With reference to FIGS. 6 and 7, taken in conjunction with FIG. 1, the liquid reservoir means 12 includes a primary or main liquid reservoir body portion 18 which terminates at its lower end in an annular wall 19. As can be seen in FIG. 7, the reservoir body portion 18 is generally rectangular in cross sectional configuration with rounded corners. The annular wall 19 defines an opening 20 into the interior of the reservoir body 18. An upstanding filler tube 22 is preferably formed integral with the reservoir body portion 18, as through a connecting web 24, and extends along the longitudinal length of the reservoir body portion 18. The upstanding filler tube 22 is connected at its lower end to the annular wall 19 in communication with the opening 20, and has a sealed upper end surface 26 which extends above the top of the reservoir body 18. An external right-hand thread 28 is formed on the outer periphery of the filler tube 22 adjacent its upper sealed end 26 to provide a threaded end upon which the adapter head means 14 may be threadedly engaged. The sealed end 26 of the filler tube 22 is pierceable by a piercing element provided on the adapter head means 14 as will be described more fully hereinbelow.

The upper end 28 of the reservoir body 18 has an opening 30 formed therein which terminates in an upwardly extending integral cap portion 32. The cap portion 32 has an upstanding cylindrical tubular extension 34 formed integral thereon which has an upper closed end 36 and a radially outwardly extending connector nib 38. The connector nib 38 has annular ridges 40a, 40b and 40c formed thereon which are of progressively increasing diameter and which serve to receive and retain the end of a rubber or suitable elastomeric drain tube 42 (FIG. 1) when the humidifier-nebulizer apparatus 10 is used in a nebulizing mode of operation, and serves to receive the end of a cannula when the apparatus is used in a humidifier mode of operation.

The liquid reservoir means 12 is preferably formed of a polyolefin material which lends itself to conventional blow molding techniques. The liquid reservoir means 12, as illustrated in FIG. 6, may be made by known "blowing and filling" methods and machinery. In blow molding the liquid reservoir 12, the reservoir body 18 and filler tube 22 are initially formed, with the upper end 26 of the filler tube being formed integral during the blowing process. During the blow molding process, a sparger, which may alternatively be termed a diffuser, and which is indicated generally at 44, is held in position between the mold halves on locating pins and molded in-place.

The sparger 44 includes a lower circular nonporous base plate portion 46 which has an annular knurled flange 48 about which the wall 19 is formed. The sparger 44 also includes a circular planar sparger plate 60 which has a depending annular wall 62 formed integral therewith. The lower edge of the depending wall 62 seats against an annular recessed surface 66 formed on the base plate 46. A radial flange 64 is formed adjacent the periphery of the sparger plate 60, and the wall 19 is formed about this flange to retain the sparger plate 60 in place. The wall 62 is spaced radially inwardly from the wall 19 so as to define an annular passage 67 therebetween which is in open fluid communication with the lower end of the filler tube 22. The wall 62 has a plurality of openings 68 formed therein to provide communication between the annular passage 67, and thus the lower end of the filler tube 22, and the interior of the sparger 44. In the illustrated embodiment, three rectangular openings 68 are provided in equidistantly spaced relation about the wall 62.

After blow forming the liquid reservoir body 18 and filler tube 22, with the sparger 44 formed in-place within the annular wall 19, a sterilized liquid, such as water 50, may be introduced through the reservoir opening 30 prior to forming the integral cap portion 32 and upstanding extension 34. After liquid is introduced into the reservoir 18, the blowing machine forms the cap 32, the upstanding extension 34, the connecting nip 38 and a rectangular tab 52 onto the upper end 28 of the liquid reservoir adjacent the opening 30. In this manner, total sealing of the liquid 50 within the liquid reservoir means 12 is accomplished. The tab 52 may subsequently be broken off from the connecting nib 38 to expose the internal bore 54 of the connecting nib. The interior of the reservoir 18 may then be connected through nib 38 to the drain tube 42, as shown in FIG. 1, or to a cannula.

The sparger plate 60 of the sparger 44 has a plurality of openings 70 formed therein in a radial spoke-like pattern as shown in FIG. 7. Each of the openings 70 has an upwardly diverging frustoconical upper end 70a. As gas, such as oxygen, is introduced into the upper end of the filler tube 22, it pushes the liquid within the filler tube downwardly and into the reservoir 18. The gas thus passing downwardly within the filler tube passes through the openings 68 in the sparger 44 and upwardly through the openings 70 in the sparger plate 60 where the gas reacts against the liquid surface and forms bubbles which pass upwardly through the liquid 50 for outward passage in a humidified state through the connector nib 38. It has been found that the sparger 44 provides quiet and efficient operation in carrying out its intended function.

The flat base plate 46 of the sparger 44 cooperates with the lower end of the annular wall 19 of reservoir 18 to provide a surface against which a heating element may be positioned to facilitate heating of the liquid within the reservoir 18 as desired.

With particular reference to FIGS. 2-5, taken in conjunction with FIG. 1, the adapter head means 14 includes an adapter body, indicated generally at 74, which has a first tubular body portion 76 having an air input end 76a upon which is mounted a regulator cap 78 to be described more fully below. The tubular body portion 76 has a second end 76b which defines an output or discharge passage 80 for the adapter head means 14 when employed in a nebulizing mode of operation.

The adapter body 74 has a tubular portion 82 which depends downwardly from and is integrally connected to the tubular portion 76 such that the axis of the tubular portion 82 is substantially transverse to the longitudinal axis of the tubular portion 76. The tubular body portion 82 has an internal thread 84 formed therein which is adapted for threaded cooperation with the external thread 28 formed on the upper end of the filler tube 22 to provide means for releasably securing the adapter head means 14 onto the liquid reservoir means 12.

The adapter body 74 has an upwardly directed tubular portion 86 which is preferably formed integral with the tubular body portion 76 and has its axis offset from but parallel to the axis of the tubular portion 82, both such axes lying in the plane of FIG. 2. The upstanding body portion 86 serves to support the control valve means 16 to be described. The tubular body portion 86 defines an internal cylindrical surface 88 which receives the outer cylindrical surface 90 of a spike member 92. The spike member 92 forms a portion of the control valve means 16 and has a lower planar surface 94 a portion 94a of which seats against a surface 96 formed on a transverse support shelf 98 formed integral with and internally of the tubular body portion 76. The spike member 92 is retained against the support surface 96 by an annular retainer lip 102 formed at the upper end of the cylindrical surface 88 to facilitate a snap-fit assembly.

The spike member 92 includes a cylindrical spike element 108 which has a lower pointed end 110. The pointed end 110 of the spike element 108 is adapted to pierce the upper end wall 26 on the filler tube 22 when the adapter head 14 is mounted on the liquid reservoir 12. Such piercing is accomplished when the tubular portion 82 of the adapter head is threaded onto the external thread 28 on the filler tube 22. An annular sealing member 111 is mounted within the tubular portion 82 of the adapter head 14 adjacent the spike end 110 for sealing engagement with the upper end 26 of the filler tube 22.

The spike element 108 has an axial flow passage 112 therein which terminates at its lower end in a transverse bore 114 intersecting the peripheral surface of the conical end 110. The upper end of the flow passage 112 terminates in a cylindrical chamber 116 formed in the spike member 92. The cylindrical chamber 116 has an upper enlarged diameter surface portion 116a which receives a valve body 118. The valve body 118 has a stepped outer cylindrical surface having a lower surface portion 118a, an intermediate surface portion 118b rotatable within the upper portion 116a of the chamber 116, and an upper surface portion 118c. The intermediate surface portion 118b of the valve body 118 has an annular rounded projection 120 formed thereon which cooperates with an annular recess 122 formed in the surface 116a to provide a snapfit assembly of the valve body 118 within the spike member 92.

The valve body 118 has a lower frustoconical surface 124 which, when the valve body 118 is assembled within the spike member 92, is spaced from a similarly configured frustoconical surface 126 formed at the lower end of the chamber 116 in the spike member 92. In assembly, the frustoconical surfaces 124 and 126 define an aspiration passage therebetween which is in flow communication with the flow passage 112 in the spike element 92. The suction action of the aspiration passage is created by the flow of gas downwardly from an axial passage 130 in the valve body 118 through a restrictive axial orifice or passage 132 in the valve body, and through an enlarged diameter flow orifice 134 formed in the spike member 92 axially aligned with orifice 132, the orifices 132 and 134 creating a venturi effect on the aspirator passage. A conical surface 136 having an included angle of approximately 90° interconnects the orifice 132 to the passage 130. A transverse passage 138 is formed in the wall of the lower portion 118a of the valve body 118 so as to be closed off by the peripheral wall surface of chamber 116 when the valve body 118 is in a rotational position as shown in FIG. 2. Rotation of the valve body 118 180° relative to its position as shown in FIG. 2 will establish communication between the axial passage 130 and the passage 112 through transverse passage 138.

The axis of the orifices 132 and 134 intersects the center of a generally spherically shaped member 140 formed on the spike element 108 below the orifice 132. The member 140 serves as an impact target for nebulized liquid-gas discharged from the orifice 134, and further breaks down the liquid particle size. It will be appreciated that the impact target 140 may take alternative shapes such as a cylindrical configuration.

The control valve means 16 includes an adjustment collar 142 to faciliate rotational movement of the valve body 118 from a position wherein the transverse flow passage 136 is closed off by the wall of chamber 116 to a position wherein the transverse passage 136 is in communication with the flow passage 112 in spike element 108. The adjustment collar 142 is rotatably mounted on the tubular portion 86 of the adapter body 74 and has a generally circular opening 144 in its upper end which receives the valve body 118 therethrough. The adjustment collar 142 has a recess 146 in the opening 144 which registers with a projection 148 formed on the valve body 118 such that rotation of the adjustment collar 142 effects a corresponding rotation of the valve body. The adjustment collar 142 has a depending wall or skirt 150 the lower inner surface of which has an annular rib 152 adapted for snap-on relation with an annular outwardly projecting rib 154 formed on the upstanding adapter body portion 86. A thumb piece 156 is formed on the depending wall 150 of the adjustment collar 142 to facilitate rotation of the adjustment collar.

The adjustment collar 142 has a radially inwardly directed rib 158 formed on the inner surface of wall 150 for registration with either one of two recesses 160 and 162 formed on the peripheral surface of the adapter body portion 86. In this manner, the adjustment collar may be selectively positioned on the adapter body in either of two rotational positions approximately 180° apart. The adapter body 74 is preferably marked adjacent the two alternative positions of the thumb piece 156 so that the operator knows whether the control valve means 16 is in a nebulizing or humidifying position.

During operation, the adapter head means 14 is connected to a source of oxygen or other gas (not shown) in a manner to introduce the gas into the bore 130 in the valve body 118. To facilitate such connection to an external source of gas, an adapter nut 164 is retained on the upper end of the valve body 118 and has internal threads 166 for threaded connection with a conventional fitting on a gas supply tube (not shown). The adapter nut 164 has external ribs 168 thereon to facilitate rotation of the adapter nut and has an internal configuration conforming to an annular projection 170 on the valve body 118 to effect a sealing connection with a fitting of the external source of gas.

With the adapter head means 14 threadedly mounted on the upper end of the filler tube 22 of a liquid reservoir 12 such that the spike element 108 pierces the upper end 26 of the filler tube, and with the adapter nut 146 connecting the control valve means 16 to a source of oxygen or other gas, the humidifier-nebulizer apparatus may be used in either a humidifying or a nebulizing mode of operation. With the control valve 16 positioned as shown in FIG. 2, gas introduced under sufficient pressure into the flow passage 130 in the valve body 118 causes the gas to pass through the venturi established by orifices 132 and 134. The venturi action of the gas passing through these orifices causes liquid from the liquid reservoir 12 to be drawn upwardly from the filler tube 22 through the flow passage 112 in the spike element 108 and through the aspiration passage for intermixing with the gas passing through the orifices 132 and 134. The liquid-gas mixture thus formed impinges the sphere 140 whereupon the liquid particles carried with the gas are further reduced in size to small mist particles. The nebulized liquid-gas mixture is then passed outwardly from the adapter head means 14 through the outlet passage 80.

A connector 172 may be mounted on the tubular end 76b of the adapter body 74 through a snap-fit connection at 174. The connector 172 has an outer end portion 176 for connection to the tube of an oxygen mask, oxygen tent or other means used by a person undergoing inhalation therapy. The connector 176 has a tubular drain connection portion 178 for connection to the end of the tube 42 opposite its connection to the connecting nib 38 on the liquid reservoir 18. During use of the apparatus 10 in a nebulizing mode of operation, any condensation formed within the outlet passage 80 will pass through the tube 42 into the liquid reservoir 18.

During operation of the humidifier-nebulizer apparatus 10 in a nebulizing mode of operation as described, it may be desirable to intermix air with the liquid-gas mixture discharged from the orifice 134. To facilitate the entry of air into the adapter head means 14, the tubular portion 76a of the adapter body 74 has a pair of generally rectangularly shaped openings 180 formed therein, as best seen in FIGS. 2 and 5. The regulator cap 78 has a pair of diametrically opposed arcuate walls 182 and 184 which extend axially inwardly into the tubular body portion 76a for sliding engagement with the inner peripheral surface thereof. The walls 182 and 184 of the regulator cap 78 are of suitable arcuate extent and axial length to allow rotation of the regulator cap 78 to selectively close-off or open the air intake openings 180 in the adapter body whereby to selectively control air drawn inwardly through the openings 180 due to the reduced pressure created by the venturi orifices 132 and 134. The regulator cap 78 is retained on the tubular portion 76a of the adapter body 74 in a snap-fit manner through an annular wall 186. Preferably, an air filter 188 of conventional construction is disposed inwardly from the air intake openings 180 in the adapter body 74 to filter air passing from the openings 180 into the outlet passage 80 of the adapter body for intermixing with nebulized liquid-gas mixture discharged form the orifice 134.

When it is desired to employ the humidifier-nebulizer apparatus 10 in a humidifying mode of operation, the tube 42 is removed and the connector nib 38 is connected directly to a cannula as may be used in inhalation therapy. The adjustment collar 142 is rotated to a position 180° from the position shown in FIG. 2 such that the transverse passage 138 in the valve body 118 is in flow communication with the passage 112 in the spike element 108. Thereafter, introduction of gas under sufficient pressure through the passage 130 in the valve body 118 will effect downward flow of the major portion of the gas into the filler tube 22 and upwardly through the openings 70 in the sparger plate 60. The gas passed upwardly through the sparger plate 60 forms small bubbles which pass upwardly through the liquid 50 and are discharged through discharge passage 54 as moistened gas particles.

When used in the humidifying mode of operation, the connector 172 is removed from the tubular end 76b of the adapter body 74 and a cap 190 (FIG. 8) is snap-fit assembled onto the end 76b. The cap 190 serves to substantially seal off the end of the passage 80 and insure flow of gas through transverse passage 138 into the liquid reservoir 18 for effecting discharge of a humidified gas through the connector nib 38.

Because the orifices 132 and 134 are not totally blocked during use in a humidifier mode of operation, some gas will be discharged from the orifice 134 into the outlet passage 80 of the adapter body. To prevent an undesirable buildup of pressure within the outlet passage 80, pressure relief means, indicated generally at 192, is provided in the regulator cap 78 to release the pressure within the outlet passage 80 when it reaches a predetermined value. The pressure relief means 192 comprises a plug-like member having a cylindrical wall 194 which is received in snap-fit relation through a circular opening 196 in the cap 78. The pressure relief means 192 has an annular inclined wall portion 198 which extends in overlying relation to the outer end of the cap 78 so as to overlie a pair of diametrically opposed flow passages 200 formed as marginal recesses in the opening 196. The annular wall 198 is of a predetermined resiliency so as to move outwardly from its contact with the end wall of the cap 78 when the pressure buildup within the passage 80 reaches a predetermined value whereupon the pressure will be relieved through the passages 200. It will be understood that the pressure within the passage 80 is a function of the pressure within the liquid reservoir 12 so that the pressure relief means 192 also serves to prevent an undesirable pressure buildup in the liquid reservoir 12.

FIG. 9 illustrates an alternative venturi arrangement for use in control valve means, indicated generally at 16', in accordance with the present invention. The elements of the embodiment of FIG. 9 which are similar to elements described above in connection with FIGS. 1–7 are represented by corresponding primed reference numerals. The spike member 92' of the embodiment of FIG. 9 is generally similar to the above described spike element 92 but differs therefrom in that it has a planar surface 204 formed at the lower end of the cylindrical chamber 116' the plane of surface 204 being normal to the longitudinal axis of chamber 116'. An axial discharge orifice 134' provides communication between the chamber 116' and the outlet passage 80' in the adapter body 74'.

The valve body 118' includes an axial bore 130' which terminates at its lower end in a cylindrical chamber 130a' which receives a cylindrically shaped venturi block member 206. The venturi block 206 has a lower surface which abuts the planar surface 204 of the chamber 116', and includes an axial venturi passage defined by a restricted intermediate flow passage 208a having frustoconical entry and exit surfaces 208b and 208c. The restricted orifice 208a communicates with an annular recess 210 about the venturi block through a transverse flow passage 212.

The valve body 118' has a lower transverse passage 214 which is in continual communication with the annular recess 210 in the venturi block 206, and has an upper transverse flow passage 216 which, when the valve body 118 is in its position as shown in FIG. 9, provides communication between the passage 130' and the axial passage 112' in the spike member 92'.

With the control valve means 16' mounted on a liquid reservoir 12 as above described, and with the valve body 118' positioned as shown in FIG. 9, gas introduced into the flow passage 130' will pass through the transverse flow passage 216 and downwardly through the flow passage 112' into the filler tube 22 where it thereafter passes upwardly through the sparger plate 60 and through the liquid 50 for discharge in a humidifying mode of operation.

Rotation of the valve body 118' through the adjustment collar 142' to a position disposed 180° from the position shown in FIG. 9 causes the transverse passage 216 to be closed off by the wall of the chamber 116'. However, the new position of the valve body 118' establishes flow communication between the transverse passage 214 and the axial passage 112' in the spike 108. Gas passing through the venturi passages 208a, b and c creates a venturi suction effect which draws liquid from the liquid reservoir 18 and filler tube 22 upwardly for intermixing with gas passing through the venturi orifice 208*a*, the mixture thereafter being discharged from orifice 134' in a nebulized liquid-gas mixture which impinges the breakdown sphere 140' and is subsequently discharged through the discharge opening 80 of the adapter head means 14'.

While preferred embodiments of the present invention have been illustrated and described, it will be obvious to those skilled in the art that changes and modifications may be made therein without departing from the invention in its broader aspects. Various features of the invention are defined in the following claims.

What is claimed is:

1. A humidifier-nebulizer apparatus for use with a source of pressurized gas, comprising, in combination, a liquid reservoir defining a primary liquid adapted to contain a quantity of liquid and having a humidifier discharge passage communicating with said primary chamber, said reservoir having an opening at its lower end defined by a generally annular wall, sparger means supported by said reservoir and including a liquid impervious bottom wall sealingly secured at its peripheral edge to said annular wall within said opening and a sparger plate spaced from said bottom wall and having a plurality of flow orifices therethrough, said sparger plate having a depending wall formed thereon the lower edge of which abuts said bottom wall, said depending wall being spaced inwardly from and parallel to said annular wall of said reservoir to define an annular passage therebetween, said depending wall having at least one opening therein, a filler tube extending generally longitudinally upwardly along said primary chamber and having a lower end connected to said annular wall such that the interior of said filler tube is in communication with said annular passage, and adapter head means mounted on said liquid reservoir, said adapter head means including a nebulizer discharge passage, a gas inlet passage connectible to a source of pressurized gas, a liquid supply passage in flow communication with the interior of said filler tube, a venturi passage in communication with said nebulizer discharge passage and said gas input passage, an aspiration passage communicating with said venturi passage and said liquid supply passage, and a bypass passage for selectively substantially bypassing input gas around said venturi passage, said adapter head being manipulatable to a first position to cause said bypass passage to be blocked such that pressurized gas introduced into said gas input passage will pass through said venturi passage and draw a liquid from said primary chamber for discharge in a nebulized gas-liquid state from said nebulizer discharge passage, said adapter head being further manipulatable to a second position wherein said bypass passage is in communication with said gas input passage and said liquid supply passage such that gas introduced into said gas input passage is caused to flow through said bypass passage and through said filler tube and sparger plate into said primary liquid chamber for discharge in a humidified state from said humidifier discharge passage.

2. A humidifier-nebulizer apparatus as defined in claim 1 wherein said adapter head means includes an air intake passage in axially aligned communication with said nebulizer discharge passage, and regulator cap means cooperative with said air intake passage to control the entry of air therethrough into said nebulizer discharge passage.

3. A humidifier-nebulizer apparatus as defined in claim 2 including air filter means disposed within said air intake passage such that air passing through said air intake passage to said nebulizer discharge passage passes through said air filter.

4. A humidifier-nebulizer apparatus as defined in claim 1 wherein said valve body includes an axial chamber therein, and wherein said venturi passage is defined by a venturi block member received within said axial chamber.

5. A humidifier-nebulizer apparatus as defined in claim 1 wherein said adapter head means includes an adapter body mountable on said liquid reservoir means, said adapter body defining said nebulizer discharge passage, and control valve means supported by said adapter body, said control valve means defining said gas input passage, said liquid supply passage, said venturi passage, said aspiration passage and said bypass passage and being manipulatable to effect either said discharge from said nebulizer discharge passage or said discharge from said humidifier discharge passage.

6. A humidifier-nebulizer apparatus as defined in claim 8 wherein said control valve means includes an impact element supported in the path of discharge of said gas-liquid mixture into said nebulizer discharge passage.

* * * * *

UNITED STATES PATENT AND TRADEMARK OFFICE
CERTIFICATE OF CORRECTION

PATENT NO. : 4,061,698
DATED : December 6, 1977
INVENTOR(S) : Everett D. Thornwald It is certified that error appears in the above-identified patent and that said Letters Patent are hereby corrected as shown below:

Column 9, line 18, Claim 1, after "liquid" insert --chamber--

Column 10, line 44, Claim 6, "Claim 8" should be --Claim 5 --

Signed and Sealed this

Eighteenth Day of July 1978

[SEAL]

Attest:

RUTH C. MASON
Attesting Officer

DONALD W. BANNER
Commissioner of Patents and Trademarks